(12) United States Patent
Florence et al.

(10) Patent No.: US 10,299,994 B2
(45) Date of Patent: *May 28, 2019

(54) COSMETIC COMPOSITIONS AND USES THEREOF

(71) Applicant: Mary Kay Inc., Addison, TX (US)

(72) Inventors: Tiffany Florence, Dallas, TX (US); Michelle Hines, Hickory Creek, TX (US); David Gan, Southlake, TX (US)

(73) Assignee: Mary Kay Inc., Addison, TX (US)

( * ) Notice: Subject to any disclaimer, the term of this patent is extended or adjusted under 35 U.S.C. 154(b) by 185 days.

This patent is subject to a terminal disclaimer.

(21) Appl. No.: 15/283,884

(22) Filed: Oct. 3, 2016

(65) Prior Publication Data

US 2017/0020806 A1   Jan. 26, 2017

Related U.S. Application Data

(63) Continuation of application No. 14/204,553, filed on Mar. 11, 2014, now Pat. No. 9,463,155.
(Continued)

(51) Int. Cl.
*A61K 36/02* (2006.01)
*A61K 36/03* (2006.01)
*A61K 36/04* (2006.01)
*A61K 36/05* (2006.01)
*A61K 8/04* (2006.01)
*A61K 8/97* (2017.01)
(Continued)

(52) U.S. Cl.
CPC .............. *A61K 8/04* (2013.01); *A61K 8/365* (2013.01); *A61K 8/4953* (2013.01); *A61K 8/602* (2013.01); *A61K 8/922* (2013.01); *A61K 8/97* (2013.01); *A61K 8/9706* (2017.08); *A61Q 19/06* (2013.01)

(58) Field of Classification Search
CPC ........ A61K 36/02; A61K 36/03; A61K 36/04; A61K 36/05
USPC ......................................................... 424/725
See application file for complete search history.

(56) References Cited

U.S. PATENT DOCUMENTS 2,798,053 A   7/1957   Brown ............................ 521/38
3,755,560 A   8/1973   Dickert et al. ............. 514/772.6
(Continued)

FOREIGN PATENT DOCUMENTS

CN   1378441   11/2002
CN   1512889   7/2004
(Continued)

OTHER PUBLICATIONS

Search Report from Chinese Application No. 2014800156658, dated Nov. 24, 2016.
(Continued)

*Primary Examiner* — Christopher R Tate
(74) *Attorney, Agent, or Firm* — Norton Rose Fulbright US LLP

(57) ABSTRACT

Disclosed is a method for reducing the appearance of cellulite or improving the texture of skin in a target region of skin that has cellulite or rough skin texture, the method comprising topically applying a composition to the target region that includes an effective amount of a mixture of caffeine, escin, and an aqueous-alcoholic extract from *Ascophyllum nodosum*, wherein topical application of the composition reduces the appearance of cellulite or improves the texture of the skin.

18 Claims, 5 Drawing Sheets

Related U.S. Application Data

(60) Provisional application No. 61/877,731, filed on Sep. 13, 2013, provisional application No. 61/788,195, filed on Mar. 15, 2013.

(51) Int. Cl.

| | | |
|---|---|---|
| *A61K 8/365* | (2006.01) | |
| *A61K 8/49* | (2006.01) | |
| *A61K 8/60* | (2006.01) | |
| *A61Q 19/06* | (2006.01) | |
| *A61K 8/92* | (2006.01) | |
| *A61K 8/9706* | (2017.01) | |

(56) References Cited

U.S. PATENT DOCUMENTS

| | | | |
|---|---|---|---|
| 4,421,769 A | 12/1983 | Dixon et al. | 514/772 |
| 4,509,949 A | 4/1985 | Huang et al. | 8/558 |
| 4,599,379 A | 7/1986 | Flesher et al. | 524/801 |
| 4,628,078 A | 12/1986 | Glover et al. | 526/303.1 |
| 4,835,206 A | 5/1989 | Farrar et al. | 524/457 |
| 4,849,484 A | 7/1989 | Heard | 525/221 |
| 5,011,681 A | 4/1991 | Ciotti et al. | 510/136 |
| 5,087,445 A | 2/1992 | Haffey et al. | 424/59 |
| 5,100,660 A | 3/1992 | Hawe et al. | 424/78.35 |
| 5,411,744 A | 5/1995 | Hill et al. | 424/450 |
| 5,508,033 A | 4/1996 | Briand | 424/195.17 |
| 5,561,158 A | 10/1996 | Yu et al. | 514/557 |
| 5,612,038 A | 3/1997 | Gedouin et al. | 424/195.17 |
| 5,804,203 A | 9/1998 | Hahn et al. | 424/401 |
| 5,843,911 A | 12/1998 | Nakahara et al. | 514/38 |
| 5,958,436 A | 9/1999 | Hahn et al. | 424/401 |
| 6,159,480 A | 12/2000 | Tseng et al. | 424/401 |
| 6,203,802 B1 | 3/2001 | Handjani et al. | 424/401 |
| 6,387,398 B1 | 5/2002 | Vollhardt et al. | 424/450 |
| 6,767,924 B2 | 7/2004 | Yu et al. | 514/557 |
| 7,105,184 B2 | 9/2006 | Pauly et al. | 424/725 |
| 7,737,186 B2 | 6/2010 | Franchi et al. | 514/738 |
| 7,871,766 B2 | 1/2011 | Pauly et al. | 435/6.16 |
| 9,463,155 B2 * | 10/2016 | Florence | A61K 8/975 |
| 2004/0109905 A1 | 6/2004 | Bagchi | 424/732 |
| 2004/0208902 A1 | 10/2004 | Gupta et al. | 424/401 |
| 2004/0219124 A1 | 11/2004 | Gupta et al. | 424/70.13 |
| 2005/0163880 A1 | 7/2005 | Pusateri et al. | 424/777 |
| 2007/0141012 A1 | 6/2007 | Cho et al. | 424/70.13 |
| 2007/0166405 A1* | 7/2007 | Song | A61K 36/185 424/725 |
| 2008/0193399 A1 | 8/2008 | Alleon | 424/61 |
| 2008/0317879 A1* | 12/2008 | Jung | A61K 36/346 424/725 |
| 2009/0117061 A1 | 5/2009 | Gross | 424/29 |
| 2009/0215720 A1 | 8/2009 | Thibodeau et al. | 514/54 |
| 2009/0280150 A1 | 11/2009 | Kamen et al. | 424/401 |
| 2010/0227830 A1 | 9/2010 | Grassauer et al. | 514/33 |
| 2011/0081430 A1 | 4/2011 | Kaur et al. | 424/764 |
| 2011/0111063 A1 | 5/2011 | Yokozeki | 424/725 |
| 2011/0150786 A1 | 6/2011 | Desenne et al. | 424/47 |
| 2011/0158922 A1 | 6/2011 | Dupont et al. | 424/59 |
| 2011/0280962 A1 | 11/2011 | Bellipanni | 424/642 |
| 2012/0045531 A1 | 2/2012 | Mahmood et al. | 424/769 |
| 2012/0064136 A1 | 3/2012 | Baker et al. | 424/401 |
| 2012/0064173 A1 | 3/2012 | Kizoulis et al. | 424/630 |
| 2012/0195870 A1 | 8/2012 | Herrmann et al. | 424/94.1 |
| 2012/0288478 A1 | 11/2012 | Florence et al. | 424/93.1 |
| 2013/0017239 A1 | 1/2013 | Viladot et al. | 424/401 |
| 2013/0149398 A1* | 6/2013 | Yesudas | A61K 36/90 424/726 |
| 2013/0216596 A1 | 8/2013 | Viladot et al. | 424/401 |

FOREIGN PATENT DOCUMENTS

| | | |
|---|---|---|
| CN | 1638717 | 7/2005 |
| DE | 102008028822 | 2/2009 |
| EP | 1813310 | 8/2007 |
| FR | 2490492 | 3/1982 |
| FR | 2715070 | 7/1995 |
| FR | 2837386 A1 * | 9/2003 |
| WO | WO 01/17498 | 3/2001 |
| WO | WO 03/006009 | 1/2003 |

OTHER PUBLICATIONS

Cao, G. et al. "Oxygen-Radical Absorbance Capacity Assay for Antioxidants." *Free Radical Biology and Medicine*. vol. 14, Issue 3, pp. 303-311. 1993.

International Cosmetic Ingredient Dictionary and Handbook, 12th Edition, 2008, vol. 2, p. 2399.

International Cosmetic Ingredient Dictionary and Handbook, 12th Edition, 2008, vol. 1, p. 655.

Khan, M.H. et al. "Treatment of Cellulite: Part I. Pathophysiology." *Journal of the American Academy of Dermatology*. vol. 62, Issue 3, pp. 361-370. 2010.

Search Report and Written Opinion issued in PCT/US2014/023569, dated Jul. 25, 2014.

Extended European Search Report issued in European Patent Application No. 14771111.3, dated Jul. 20, 2016.

* cited by examiner

COSMETIC COMPOSITIONS AND USES THEREOF

CROSS REFERENCE TO RELATED APPLICATIONS

This application is a continuation of U.S. application Ser. No. 14/204,553, filed Mar. 11, 2014, which claims the benefit of U.S. Provisional Application No. 61/877,731, filed Sep. 13, 2013, and U.S. Provisional Application No. 61/788,195, filed Mar. 15, 2013. The contents of the referenced applications are incorporated into the present application by reference.

BACKGROUND OF THE INVENTION

A. Field of the Invention

The present invention generally relates to methods and compositions useful for treating skin conditions. More specifically, the present invention concerns topical skin care compositions that include *Rubus fruticosus* extract, *Argania spinosa* kernel oil, *Coleus barbatus* extract, glycolic acid, and a mixture of caffeine, escin, and algae extract and methods of reducing the appearance of cellulite with such compositions.

B. Description of Related Art

Humans are increasingly sensitive regarding their physical appearance. One component of physical appearance is skin texture and tone. Almost all female individuals develop fatty tissue deposits in the subcutaneous tissue layers deep under the skin which extend or project into the skin called cellulite, which manifests in an undesirable dimpled or bumpy appearance or texture of the skin. Numerous therapies for the treatment of cellulite are available, but empirical evidence for the efficacy of these strategies is limited (Khan 2010).

Therefore, new and effective treatments are needed.

SUMMARY OF THE INVENTION

The inventors found a solution to the aforementioned problems. This solution is premised on the use of particular combination of ingredients that synergistically work together to reduce the appearance of cellulite and improve skin texture.

In one embodiment, there is disclosed methods for reducing the appearance of cellulite or improving the texture of skin in a target region of skin that has cellulite or rough skin texture, the method comprising topically applying a composition to said target region that includes an effective amount of *Rubus fruticosus* extract, *Argania spinosa* kernel oil, *Coleus barbatus* extract, glycolic acid, and a mixture of caffeine, escin, and algae extract, wherein topical application of the composition reduces the appearance of cellulite or improves the texture of the skin. In particular aspects, the *Rubus fruticosus* extract is an aqueous-ethanolic extract and the algae extract is *Ascophyllum nodosum* aqueous-alcoholic extract. In some embodiments, the method further comprises increasing the skin firmness or elasticity in said target region. In some embodiments, the method comprises improving the texture of skin. In some embodiments, the composition increases lipolysis in adipocytes. In some embodiments, the composition decreases maturation of fat cells. In some embodiments, the composition increases the rate of skin renewal. In even other embodiments, the composition is capable of decreasing the size of adipocytes in the region in which the composition is applied. The composition is capable of decreasing the size of adipocytes in the target region having a diameter of equal to or greater than 40 μm or have a diameter between 40-160 μm. At least 5, 10, 15, 20, 25, 30, 35, 40, 45, 50, 60, 70, 80, 90, or 95%, or between 5 and 20%, or between 5 and 10% of the adipocytes in the target region having a diameter of equal to or greater than 40 μm or have a diameter between 40-160 μm can be decreased in size. In other aspects, the composition is capable of increasing the epidermal thickness of skin in the target region such as by at least 5, 10, 15, 20, 25, 30, 35, 40, 45, 50, 60, 70, 80, 90, or 95%, or between 5 and 50%, or 10 and 40%, or 15 and 30%. The composition can also increase triglyceride release from adipocytes in the target region such as by at least 10, 20, 30, 40, 50, 60, 70, 80, 90, 100, 150, or 200% or more.

Cellulite is the herniation of subcutaneous fat within fibrous connective tissue, which manifests in an undesirable dimpled or bumpy appearance to the skin. In some embodiments, the cellulite is characterized by skin dimpling. The texture of skin that has cellulite or rough skin texture in the target region may be dimpled, bumpy, and/or have an orange peel or cottage cheese-like texture. In some embodiments, the composition reduces the appearance, depth, or severeness of the skin dimpling. In some embodiments, the composition decreases the presence or severeness of dimples, bumps, and/or orange peel or cottage cheese-like texture. In some embodiments, the composition reduces the difference between the peak and valley of a dimple. In some embodiments, the composition results in skin which has a smoother or flatter appearance.

In one embodiment, there is disclosed a composition comprising *Rubus fruticosus* extract, *Argania spinosa* kernel oil, *Coleus barbatus* extract, glycolic acid, caffeine, escin, and *Ascophyllum nodosum* extract. The extract from *Rubus fruticosus* and/or *Coleus barbatus* may be an aqueous, alcoholic, hydro-alcoholic, or oil-based extract. In some embodiments, the *Rubus fruticosus* extract is an aqueous extract. The extract from *Rubus fruticosus* and/or *Coleus barbatus* may be from the whole plant, leaf, seed, flower, stem, or root. In some embodiments, the *Rubus fruticosus* extract is from the leaf. In some embodiments, the *Coleus barbatus* extract is from the root.

The composition can include 0.0001 to 10% by weight (or 0.001, 0.01, 0.1, 1, 2, 3, 4, 5, 6, 7, 8, 9, or 10% by weight or more) of *Rubus fruticosus* extract, 0.0001 to 10% by weight of *Argania spinosa* kernel oil (or 0.001, 0.01, 0.1, 1, 2, 3, 4, 5, 6, 7, 8, 9, or 10% by weight or more), 0.0001 to 10% by weight of *Coleus barbatus* extract (or 0.001, 0.01, 0.1, 1, 2, 3, 4, 5, 6, 7, 8, 9, or 10% by weight or more), 0.0001 to 10% by weight of glycolic acid (or 0.001, 0.01, 0.1, 1, 2, 3, 4, 5, 6, 7, 8, 9, or 10% by weight or more), and/or 0.0001 to 10% by weight of a mixture of caffeine, escin, and algae extract (or 0.001, 0.01, 0.1, 1, 2, 3, 4, 5, 6, 7, 8, 9, or 10% by weight or more).

In certain aspects, the composition is applied to the skin and remains on the skin for at least 5, 10, 15, 30, or more minutes, or 1, 4, 8, 12, 16, 20, or 24 hours after topical application. The composition can be applied to leg skin, arm skin, torso skin, or skin in the pelvic region.

The compositions of the present invention can be formulated into topical skin care compositions. The compositions can be cosmetic compositions. In other aspects, the compositions can be included in a cosmetic vehicle. Non-limiting examples of cosmetic vehicles are disclosed in other sections of this specification and are known to those of skill in the art. Examples of cosmetic vehicles include emulsions (e.g., oil-in-water and water-in-oil emulsions), creams, lotions, solutions (e.g., aqueous or hydro-alcoholic solutions), anhydrous bases (e.g., lipstick or a powder), gels, and ointments. In certain aspects, the composition can be formulated as a cream, gel, lotion, serum, or cleanser. In some instances, the composition is an emulsion (e.g., oil-in-water, water-in-oil, hydrophilic-in-hydrophobic, hydrophobic-in-hydrophilic, silicone-in-water, water-in-silicone, etc.). In one particular embodiment, the composition can be a cream-gel based composition that includes the following ingredients: water; alcohol denat.; glycerin; sorbitol; cyclopentasiloxane; dimethicone; caffeine; pentaerythrityl tetraisostearate; caprylic/capric triglyceride; pentylene glycol; ethoxydiglycol; ammonium acryloyldimethyltaurate/VP copolymer; triethanolamine; *argania spinosa* kernel oil; jojoba esters; glycolic acid; phenoxyethanol; cetyl alcohol; dipropylene glycol; maltodextrin; caprylyl glycol; cetearyl alcohol; acrylates/C10-30 alkyl acrylate crosspolymer; xanthan gum; menthyl lactate; a fragrance; *Rubus fruticosus* (Blackberry) leaf extract; *Coleus barbatus* root extract; escin; and *Ascophyllum nodosum* extract. In even more particular embodiments, the composition can include 65 to 75% by weight of water; 5 to 10 by weight of alcohol denat.; 3 to 7% by weight of glycerin; 2 to 5% by weight of sorbitol; 2 to 4% by weight of cyclopentasiloxane; 1 to 3% by weight of dimethicone; 0.5 to 2% by weight of caffeine; 0.5 to 2% by weight of pentaerythrityl tetraisostearate; 0.5 to 2% by weight of caprylic/capric triglyceride; 0.5 to 2% by weight of pentylene glycol; 0.5 to 2% by weight of ethoxydiglycol; 0.5 to 2% by weight of ammonium acryloyldimethyltaurate/VP copolymer; 0.5 to 2% by weight of triethanolamine; 0.5 to 2% by weight of *Argania spinosa* kernel oil; 0.5 to 2% by weight of jojoba esters; 0.1 to 1% by weight of glycolic acid; 0.1 to 1% by weight of phenoxyethanol; 0.1 to 1% by weight of cetyl alcohol; 0.1 to 1% by weight of dipropylene glycol; 0.1 to 1% by weight of maltodextrin; 0.1 to 1% by weight of caprylyl glycol; 0.1 to 1% by weight of cetearyl alcohol; 0.1 to 1% by weight of acrylates/C10-30 alkyl acrylate crosspolymer; 0.1 to 1% by weight of xanthan gum; 0.1 to 1% by weight of menthyl lactate; 0.1 to 1% by weight of a fragrance; 0.01 to 1% by weight of *Rubus fruticosus* (Blackberry) leaf extract; 0.01 to 1% by weight of *Coleus barbatus* root extract; 0.001 to 1% by weight of escin; and 0.001 to 1% by weight of *Ascophyllum nodosum* extract.

The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.). The compositions in non-limiting aspects can have a pH of about 6 to about 9. In other aspects, the pH can be 1, 2, 3, 4, 5, 6, 7, 8, 9, 10, 11, 12, 13, or 14. Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams. In particular aspects, the compositions can be oil-free, substantially anhydrous, and/or anhydrous. Other aspects include compositions having water.

The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

In some embodiments, reducing the appearance of cellulite or improving the texture of skin in a target region is determined by comparison of the skin in the target region that has cellulite or rough skin texture prior to application of the composition to the skin in the target region after application of the product. In some embodiments, the skin in the target region is evaluated 1, 2, 3, 4, 5, 6, or 7 days, 2, 3, 4, or 5 weeks, 2, 3, 4, 5, 6, 7, 8, 9, 10, 11, or 12 months, or any range therein, after the first application of the composition. In some embodiments, the composition is applied daily, weekly, or monthly. In some embodiments, the composition is applied 1, 2, 3, 4, or more times daily.

Additionally, the compositions can also be used to treat or prevent a variety of other skin conditions. For instance, the compositions can be used to treat or prevent a fine line or wrinkle, erythema, sensitive skin, or inflamed skin. In particular aspects, erythema, sensitive skin, or inflamed skin is caused by skin sunburn, electrical treatments of skin, skin burns, contact allergies, systemic allergies, skin toxicity, exercise, insect stings, bacterial infection, viral infection, fungal infection, protozoa infection, massage, or windburn. In other aspects, the following additional skin conditions can be treated or prevented in accordance with the methods and compositions disclosed throughout the specification and claims: pruritus, lentigo, spider veins, age spots, senile purpura, keratosis, melasma, blotches, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. The method can also include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin).

Also contemplated are kits that include any one of the compositions disclosed throughout the specification and claims. In certain embodiments, the composition is comprised in a container. The container can be a bottle, dispenser, or package. The container can dispense a predetermined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, or an anti-aging product.

Also disclosed are the following Embodiments 1 to 49 of the present invention. Embodiment 1 is a method for reducing the appearance of cellulite or improving the texture of skin in a target region of skin that has cellulite or rough skin texture, the method comprising topically applying a composition to the target region that includes an effective amount of *Rubus fruticosus* extract, *Argania spinosa* kernel oil, *Coleus barbatus* extract, glycolic acid, and a mixture of caffeine, escin, and algae extract, wherein topical application of the composition reduces the appearance of cellulite or improves the texture of the skin. Embodiment 2 is the method of Embodiment 1, further comprising increasing the skin firmness or elasticity in said target region. Embodiment 3 is the method of any one of Embodiments 1-2, wherein the composition increases lipolysis in adipocytes. Embodiment 4 is the method of any one of Embodiments 1-3, wherein the composition decreases maturation of fat cells. Embodiment 5 is the method of any one of Embodiments 1-4, wherein the composition increases the rate of skin renewal. Embodiment 6 is the method of Embodiment 1, wherein the cellulite is characterized by skin dimpling. Embodiment 7 is the method of Embodiment 6, wherein the composition reduces the appearance, depth, or severeness of the skin dimpling. Embodiment 8 is the method of any of Embodiments 1-7, wherein the composition decreases the presence or severeness of dimples, bumps, and/or orange peel or cottage cheese-like texture. Embodiment 9 is the method of any of Embodiments 1-8, wherein the composition reduces the difference between the peak and valley of a dimple. Embodiment 10 is the method of any of Embodiments 1-9, wherein the composition results in skin which has a smoother or flatter appearance. Embodiment 11 is the method of any of Embodiments 1-10, wherein roughness of the skin texture in the target area is decreased when compared to the roughness of the skin in the target area before application. Embodiment 12 is the method of Embodiment 1, wherein the *Rubus fruticosus* extract is an aqueous extract. Embodiment 13 is the method of any one of Embodiments 1-12, wherein the *Rubus fruticosus* extract is from the leaf Embodiment 14 is the method of any one of Embodiments 1-13, wherein the *Coleus barbatus* extract is from the root. Embodiment 15 is the method of any one of Embodiments 1-14, wherein the composition is formulated as a cream, lotion, emulsion, serum, or cleanser. Embodiment 16 is the method of any one of Embodiments 1-15, wherein the composition is an oil-in-water emulsion or a water-in-oil emulsion. Embodiment 17 is the method of any one of Embodiments 1-16, wherein an effective amount is 0.001 to 10% by weight of *Rubus fruticosus* extract, 0.001 to 10% by weight of *Argania spinosa* kernel oil, 0.001 to 10% by weight of *Coleus barbatus* extract, 0.001 to 10% by weight of glycolic acid, and 0.001 to 10% by weight of the mixture of caffeine, escin, and algae extract. Embodiment 18 is the method of any one of Embodiments 1-17, wherein the skin is leg skin, arm skin, torso skin, or skin in the pelvic region. Embodiment 19 is the method of any one of Embodiments 1-18, wherein the composition is applied to the skin and remains on the skin for at least 5 minutes after topical application. Embodiment 20 is the method of any one of Embodiments 1-19, wherein the composition further comprises at least one of a moisturization agent, a UV absorbing agent, anti-oxidant, structuring agent, emulsifier, silicone containing compound, essential oil, thickening agent, and a preservative. Embodiment 21 is the method of any one of Embodiments 1-20, wherein the composition further comprises a pharmaceutical ingredient. Embodiment 22 is the method of any one of Embodiments 1-21, wherein the composition decreases the size of adipocytes in the target region. Embodiment 23 is the method of Embodiment 22, wherein the composition decreases the size of adipocytes in the target region having a diameter of equal to or greater than 40 μm or have a diameter between 40-160 μm. Embodiment 24 is the method of Embodiment 23, wherein at least 5, 10, 15, 20, 25, 30, 35, 40, 45, 50, 60, 70, 80, 90, or 95%, or between 5 and 20%, or between 5 and 10% of the adipocytes in the target region having a diameter of equal to or greater than 40 μm or have a diameter between 40-160 μm are decreased in size. Embodiment 25 is the method of any one of Embodiments 1-24, wherein the composition increases the epidermal thickness of skin in the target region. Embodiment 26 is the method of Embodiment 25, wherein the composition increases the epidermal thickness of skin in the target region by at least 5, 10, 15, 20, 25, 30, 35, 40, 45, 50, 60, 70, 80, 90, or 95%, or between 5 and 50%, or 10 and 40%, or 15 and 30%. Embodiment 27 is the method of any one of Embodiments 1 to 26, wherein the composition increases triglyceride release from adipocytes in the target region. Embodiment 28 is the method of Embodiment 27, wherein the composition increases triglyceride release from adipocytes in the target region by at least 10, 20, 30, 40, 50, 60, 70, 80, 90, 100, 150, or 200%. Embodiment 29 is the method of any one of Embodiments 1 to 28, wherein the *Rubus fruticosus* extract is from the leaf, the *Coleus barbatus* extract is from the root, and the algae extract is *Ascophyllum nodosum* extract. Embodiment 30 is a topical skin composition comprising *Rubus fruticosus* extract, *Argania spinosa* kernel oil, *Coleus barbatus* extract, glycolic acid, and a mixture of caffeine, escin, and algae extract. Embodiment 31 is the topical skin composition of Embodiment 30, wherein the *Rubus fruticosus* extract is an aqueous extract. Embodiment 32 is the topical skin composition of any one of Embodiments 30-31, wherein the *Rubus fruticosus* extract is from the leaf. Embodiment 33 is the topical skin composition of any one of Embodiments 30-32, wherein the *Coleus barbatus* extract is from the root. Embodiment 34 is the topical skin composition of any one of Embodiments 30-33, wherein the composition is formulated as a cream, lotion, emulsion, serum, or cleanser. Embodiment 35 is the topical skin composition of any one of Embodiments 30-34, wherein the composition is an oil-in-water emulsion or a water-in-oil emulsion. Embodiment 36 is the topical skin composition of any one of Embodiments 30-35, wherein an effective amount is 0.001 to 10% by weight of *Rubus fruticosus* extract, 0.001 to 10% by weight of *Argania spinosa* kernel oil, 0.001 to 10% by weight of *Coleus barbatus* extract, 0.001 to 10% by weight of glycolic acid, and 0.001 to 10% by weight of the mixture of caffeine, escin, and algae extract. Embodiment 37 is the topical skin composition of any one of Embodiments 30-36, wherein the composition further comprises at least one of a moisturization agent, a UV absorbing agent, anti-oxidant, structuring agent, emulsifier, silicone containing compound, essential oil, thickening agent, and a preservative. Embodiment 38 is the topical skin composition of any one of Embodiments 30-37, wherein the composition further comprises a pharmaceutical ingredient. Embodiment 39 is the topical skin composition of any one of Embodiments 30-38, wherein the composition is capable of increasing lipolysis in adipocytes. Embodiment 40 is the topical skin composition of any one of Embodiments 30-39, wherein the composition is capable of decreasing maturation of fat cells. Embodiment 41 is the topical skin composition of any one of Embodiments 30-40, wherein the composition is capable of increasing the rate of skin renewal. Embodiment 42 is the topical skin composition of any one of Embodiments 30-41, wherein the composition is capable of decreasing the size of adipocytes. Embodiment 43 is the topical skin composition of any one of Embodiments 30-42, wherein the composition is capable of decreasing the size of adipocytes in the target region having a diameter of equal to or greater than 40 μm or have a diameter between 40-160 μm. Embodiment 44 is the topical skin composition of Embodiment 43, wherein at least 5, 10, 15, 20, 25, 30, 35, 40, 45, 50, 60, 70, 80, 90, or 95%, or between 5 and 20%, or between 5 and 10% of the adipocytes in the target region having a diameter of equal to or greater than 40 μm or have a diameter between 40-160 μm are decreased in size. Embodiment 45 is the topical skin composition of any one of Embodiments 30-44, wherein the composition is capable of increasing the epidermal thickness of skin in the target region. Embodiment 46 is the topical skin composition of Embodiment 45, wherein the composition is capable of increasing the epidermal thickness of skin in the target region by at least 5, 10, 15, 20, 25, 30, 35, 40, 45, 50, 60, 70, 80, 90, or 95%, or between 5 and 50%, or 10 and 40%, or 15 and 30%. Embodiment 47 is the topical skin composition of any one of Embodiments 30-46, wherein the composition is capable of increasing triglyceride release from adipocytes in the target region. Embodiment 48 is the topical skin composition of Embodiment 47, wherein the composition is capable of increasing triglyceride release from adipocytes in the target region by at least 10, 20, 30, 40, 50, 60, 70, 80, 90, 100, 150, or 200%. Embodiment 49 is the topical skin composition of any one of Embodiments 30-48, wherein the *Rubus fruticosus* extract is from the leaf, the *Coleus barbatus* extract is from the root, and the algae extract is *Ascophyllum nodosum* extract.

The compositions and methods for their use can "comprise," "consist essentially of," or "consist of" any of the ingredients disclosed throughout the specification. As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

"Consisting essentially of" means that inclusion of additional ingredients in the compositions do not materially affect the beneficial properties of the compositions as compositions for reducing the appearance of cellulite and improving skin texture. For instance, if a composition "consists essentially of" any one of, any combination of, or 2, 3, 4, or 5 of *Rubus fruticosus* extract, *Argania spinosa* kernel oil, *Coleus barbatus* extract, glycolic acid, and a mixture of caffeine, escin, and algae extract, said composition excludes any ingredients that would materially affect the beneficial properties of the compositions for reducing the appearance of cellulite and improving skin texture.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant. "Pharmaceutically elegant" and/or "cosmetically elegant" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting," "reducing," "treating," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
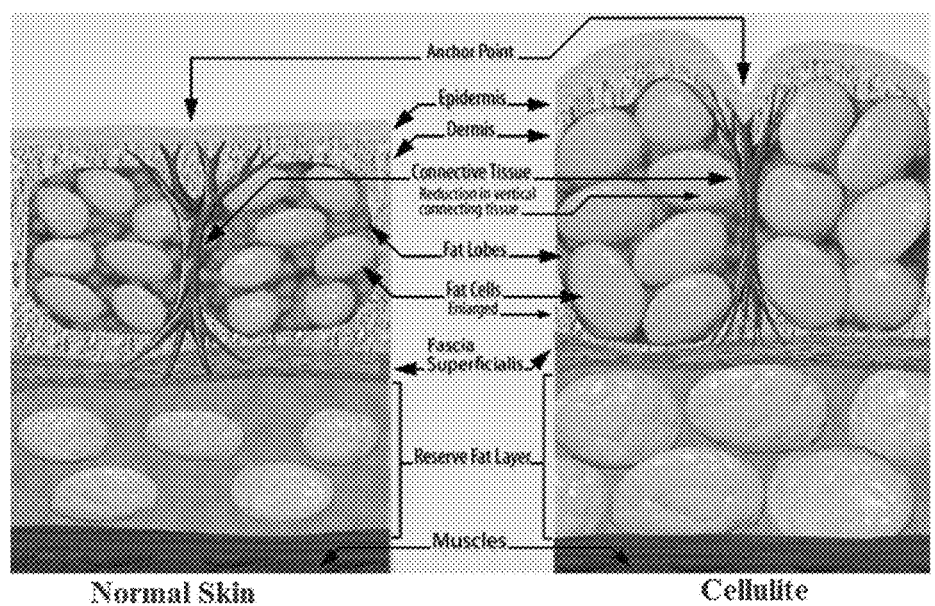
FIG. 1 Explanation of the formation of cellulite.

Cellulite (also known as adiposis edematosa, dermopanniculosis deformans, status protrusus cutis, gynoid lipodystrophy, orange peel syndrome, and cottage cheese skin) is the herniation of subcutaneous fat within fibrous connective tissue that manifests topographically as skin dimpling and nodularity, often on the pelvic region, lower limbs, and abdomen. The causes of cellulite include changes in metabolism, physiology, dieting too hard or too much, sex-specific dimorphic skin architecture, alteration of connective tissue structure, hormonal factors, genetic factors, the microcirculatory system, the extracellular matrix, and subtle inflammatory alterations. FIG. 1 provides an explanation of the formation of cellulite on a cellular level. Numerous therapies for the treatment of cellulite are available, but empirical evidence for the efficacy of these strategies is limited (Khan 2010).

The present invention is an effective alternative to the use of compositions and ingredients currently used to reduce the appearance of cellulite, improve the texture of skin, and to treat other skin conditions. As discussed above, the inventors discovered that a unique combination of ingredients provide synergistic effects in reducing the appearance of cellulite and improving the texture of the skin by reducing skin roughness and/or texture. The inventors found that the composition increases lipolysis in adipocytes, decreases maturation of fat cells, and increases the rate of skin renewal.

These and other non-limiting aspects of the present invention are described in further detail below.

A. Active Ingredients

*Rubus fruticosus* is a fruit producing plant that is found throughout the temperate Northern Hemisphere and South America. The extract can be obtained from the whole plant, the root, the flower, the stem, the leaf, the flower/leaf/stem, or the leaf/root. In particular aspects, the extract is an aqueous-ethanolic extract. Such extracts are commercially available from a wide range of sources (see, e.g., International Cosmetic Ingredient Dictionary and Handbook, 12$^{th}$ Edition, 2008 ("CTFA"), Volume 2 page 2399, which is incorporated by reference). In particular embodiments, the leaf extract is used. In some embodiments, the extract is an aqueous extract. *Rubus fruticosus* extract can be purchased from Symrise (Germany) under the trade name SymMatrix®, which is an aqueous-ethanolic extract from the leaf of *Rubus fruticosus*.

*Argania spinosa* is a species of the Argan tree, which is native to the Mediterranean region. The oil is from derived from the kernel of the fruit of the Argan tree. Such extracts are commercially available from a wide range of sources (see, e.g., CTFA, Volume 1, page 198, which is incorporated by reference). *Argania spinosa* kernel oil can be purchased from BASF (USA) under the trade name Lipofructyl Argan®. Product literature states that this ingredient is rich in poly-unsaturated fatty acids including linoleic acid, omega-6), and natural tocopherols.

*Coleus barbatus*, also commonly known as *Coleus forskohlii*, is a tropical perennial plant that is native to the lower elevations of India. The extract can be obtained from the whole plant, the root, the flower, the stem, the leaf, the flower/leaf/stem, or the leaf/root. It contains an active ingredient forskolin. In some particular embodiments, the extract from the roots is used. Such extracts are commercially available (see, e.g., CTFA, Volume 1, pages 655, which is incorporated by reference). *Coleus barbatus* extract can be purchased from Actives International (USA) under the trade name Via Pure® *Coleus*, which is an extract from the root of *Coleus barbatus*.

Glycolic acid is the smallest α-hydroxy acid (AHA). It is highly soluble in water and has the formula:

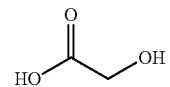

It too is commercially available from a wide range of sources (see, e.g., CTFA, Volume 1, page 1095, which is incorporated by reference).

As for the mixture of caffeine, escin, and algae extract, such a mixture is available from Rovi GMBH (Germany) under the trade name Rovisome® F.E.C. This mixture contains a combination of the blood vessel strengthening escin and the anticoagulant fucoidan. The Rovisome® F.E.C. product is a combination of water, alcohol, lecithin, escin, *Ascophyllum nodosum* extract (aqueous-alcoholic extract), caffeine. In some embodiments, the algae extract is *Ascophyllum nodosum* extract via an aqueous-alcoholic extractant.

In addition to the commercially available extracts identified above, said extracts can be produced by obtaining the corresponding plant or portion thereof to produce the extract by extraction methods which are known to those of ordinary skill in the art. For instance, a person of ordinary skill in the art would be able to isolate any one of the extracts identified above from the whole plant or parts (e.g., leaf, root) of the corresponding plant by using any suitable method known in the art. In one non-limiting example, the plant (or any part of the plant) can be disrupted by mechanical means which results in a puree. The puree is then processed to be substantially free of impurities or undesired solids. The puree can then be poured into a shallow vessel and quickly exposed to low temperature, i.e., flash frozen, for example at −20° C. or lower, preferably under a vacuum for removal of water content (lyophilization). The resultant extract can then be used in the compositions of the present invention.

In other aspects, aqueous, alcoholic, aqueous-alcoholic, or oil based extraction techniques, or combinations thereof, can be used on the whole plant or any part thereof of to produce an extract. In such a process, the desired part of the plant or the whole plant is crushed up (e.g., blender) and then subjected to a desired solvent (e.g., water, alcohol, water/alcohol, or oil based solvents) to obtain the desired extract. The extract can then be stored in liquid form, lyophilized, or subject to further processing techniques (e.g., heating, cooling, etc.). Extraction processes are well-known to those having ordinary skill in the extract field (e.g., maceration, infusion, percolation, digestion, decoction, hot continuous extraction, aqueous-alcoholic extract, counter current extract, microwave assisted extraction, ultrasound extraction, supercritical fluid extracts, phytonic extract (e.g., with hydro-flouro-carbon solvents), etc.

B. Compositions of the Present Invention

It is contemplated that the compositions of the present invention can include any of the actives or any combination thereof described throughout this specification. In particular aspects, the actives can be combined (e.g., *Rubus fruticosus* extract, *Argania spinosa* kernel oil, *Coleus barbatus* extract, glycolic acid, and a mixture of caffeine, escin, and algae extract). The compositions can include any number of combinations of additional ingredients described throughout this specification. The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.5550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

The disclosed compositions of the present invention may also include various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. In some embodiments, the compositions do not contain parabens.

C. Vehicles

The compositions of the present invention can be incorporated into all types of vehicles. Non-limiting examples of suitable vehicles include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

It is also contemplated that ingredients identified throughout this specification, including but not limited to *Rubus fruticosus* extract, *Argania spinosa* kernel oil, *Coleus barbatus* extract, glycolic acid, and a mixture of caffeine, escin, and algae extract, or any combinations thereof, can be individually or combinatorially encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver the ingredient to skin (see, e.g., U.S. Pat. Nos. 6,387,398; 6,203,802; 5,411,744; Kreuter 1998).

D. Cosmetic Products and Articles of Manufacture

The composition of the present invention can also be used in many cosmetic products including, but not limited to, sunscreen products, sunless skin tanning products, hair products, finger nail products, moisturizing creams, skin benefit creams and lotions, softeners, day lotions, gels, ointments, foundations, night creams, lipsticks, cleansers, toners, masks, or other known cosmetic products or applications. Additionally, the cosmetic products can be formulated as leave-on or rinse-off products. In certain aspects, the compositions of the present invention are stand-alone products.

E. Additional Ingredients

In addition to the *Rubus fruticosus* extract, *Argania spinosa* kernel oil, *Coleus barbatus* extract, glycolic acid, and a mixture of caffeine, escin, and algae extract, ingredients disclosed throughout this specification, compositions of the present invention can include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, ginkgo biloba, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutyiphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, *althea officinalis* extract, apricot (*prunus armeniaca*) kernel oil, arginine, arginine aspartate, *arnica montana* extract, aspartic acid, avocado (*persea gratissima*) oil, barrier sphingolipids, butyl alcohol, beeswax, behenyl alcohol, beta-sitosterol, birch (*betula alba*) bark extract, borage (*borago officinalis*) extract, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*)oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *eucalyptus globulus* oil, evening primrose (*oenothera biennis*) oil, fatty acids, *geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, *macadamia ternifolia* nut oil, maltitol, *matricaria* (*chamomilla recutita*) oil, methyl glucose sesquistearate, methylsilanol PCA, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, poly silicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several methods known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, *geranium* oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379.

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxy ethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

In Vivo Data for Skin Roughness and Elasticity

In vivo testing was performed using a composition comprising 0.5% by weight of *Rubus fruticosus* leaf extract, 0.75% by weight of *Argania spinosa* kernel oil, 0.5% by weight of *Coleus barbatus* extract, 0.8% by weight of glycolic acid, and 0.1% by weight of a mixture of caffeine, escin, and algae extract. *Rubus fruticosus* leaf extract was purchased from Symrise (Germany) under the trade name SymMatrix®, the *Argania spinosa* kernel oil was purchased from BASF (USA) under the trade name Lipofructyl Argan®, the *Coleus barbatus* extract was purchased from Actives International (USA) under the trade name Via Pure® *Coleus*, and the mixture comprising mixture of caffeine, escin, and algae extract was purchased from Rovi GMBH (Germany) under the trade name Rovisome® F.E.C. In particular, a 3-week clinical evaluation for skin roughness/texture and skin elasticity/firmness was performed using a proprietary base lotion formulation as the vehicle for the aforementioned ingredients. This set-up allowed for confirmation that the combination of ingredients can improve skin roughness and reduce the appearance of cellulite on affected skin.

Nineteen (19) female panelists between the ages of 21 to 65 years were enrolled in and completed the three week monadic study. Panelists were required to have mild to moderate cellulite on thighs. Panelists were instructed to stop using all cellulite and body treatment products and to continue using their normal basic body lotion. Panelists were instructed to apply the product onto cellulite prone areas of the thighs twice daily (AM and PM) by gently massaging the product onto the skin.

At Day 0 (baseline) and at the end of week 3 (Day 21), skin replicas were taken on the back of one thigh using Silfo resin. Skin elasticity and firmness measurements were taken using BTC on the back of a different thigh.

Figure 2A:
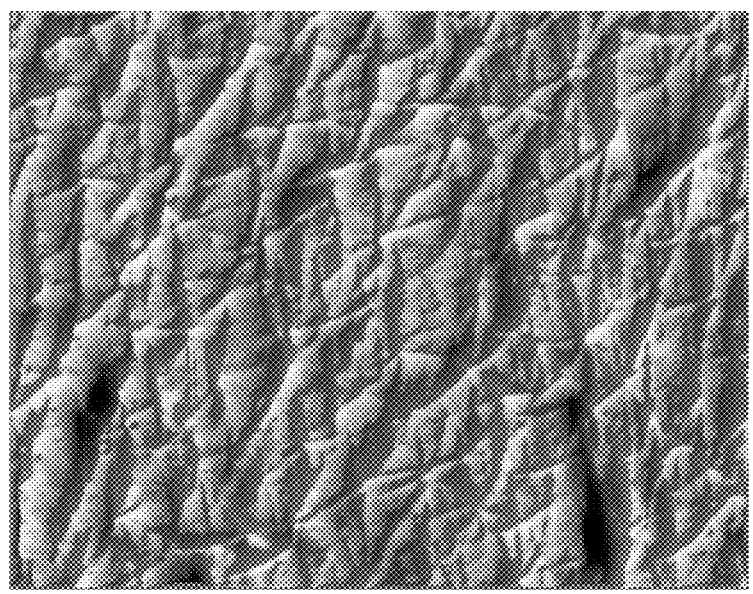
FIGS. 2A-B are photos of skin replicas taken on the back of one thigh using Silastic Replicating Resin (Silflo) resin at Day 0 (FIG. 2A) and Day 21 (FIG. 2B).
Figure 2B:
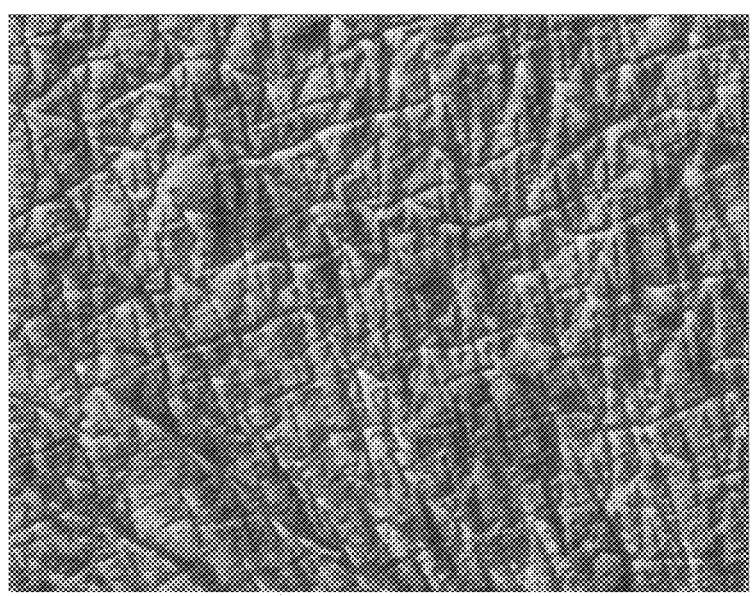

After 3 weeks, 79% of panelists showed improvement in skin roughness/texture compared to the baseline. Results are shown in Table 1, and photos of the replicas at Day 0 and Day 21 are shown in FIGS. 2 A-B.

TABLE 1

| REPLICA ANALYSIS | |
|---|---|
| Percent of Panelists Showed Improvement | |
| Compared to Baseline [Mean % Percent] | |
| | Week 3 |
| Parameter | N = 19 |
| Roughness | 79%* |
| (SRq) | [17%] |

*Significant at 95% confidence level compared to baseline

Skin elasticity: After 3 weeks, 74% of panelists showed improvement in skin elasticity compared to baseline. There was a directional improvement in skin firmness. However, it was not significant compared to baseline. Results are shown in Table 2.

TABLE 2

BTC MEASUREMENTS
Percent of Panelists Showed Improvement
Compared to Baseline [Mean % Percent]

| Parameter | Week 3<br>N = 19 |
|---|---|
| Elasticity | 74%*<br>[5%] |
| Firmness | Showed directional improvement, but it was not significant compared to baseline |

*Significant at 95% confidence level compared to baseline

Based on the results of this study, the product showed a significant improvement in skin texture and elasticity after three weeks compared to baseline. The formula is also a good predictor to pass for increase in skin elasticity after three weeks compared to baseline. Regarding the skin firmness, the results from this research study showed that it would take longer than three weeks to show significant improvement compared to baseline.

Example 2

In Vitro Data for Adipocyte Size Reduction

The same combination of actives, in the same amounts, and the same base lotion formulation from Example 1 was also used to test the ability of the combination of ingredients to reduce the size of adipocytes on human skin explants. The results of this In vitro study confirm that after 10 days of treatment the combination of actives reduced the size of adipocytes by 8% in adipocytes having a starting size of 40-160 μm and increased the size of adipocytes by 16% in adipocytes having a starting size of 0-40 μm. The protocol used to procure these data is provided below.

Explant Preparation:

6 skin explants from a subject having an average diameter of 10 mm (±1 mm) with about 0.5 cm thickness of hypodermis were prepared. The explants were kept in survival in BEM culture medium light (BIO-EC's Explants Medium Light) at 37° C. in a humid, 5%-$CO_2$ atmosphere.

Product/Lotion Application:

On days D0, D3, D4, D6, and D7, 2 mg·$cm^2$ of the lotion was topically applied to three explants with a small spatula. The remaining three explants did not receive the lotion and were therefore used as a control.

Sampling:

On day D0, 3 explants were collected and cut in two parts. One part was fixed in ordinary Bouin, the other was frozen at −80° C. On day D10, the three explants in which the lotion was applied on days D3, D4, D6, and D7, were collected and process in the same way.

Histological Processing:

After fixation for 48 hours in ordinary bouin, the samples were dehydrated and impregnated in paraffin using a using a Leica TP 1010 our TP 1020 dehydration automat according to the SOP H-149. The samples were then embedded according to SOP H-153 using a Leica EG 1160 embedding station. 5-μm-thick sections were made according to SOP H-173 using a Leica RM 2125 Minot-type microtome, and the sections were then mounted on Superfrost® histological glass slides. The frozen samples were cut into 7-μm-thick sections using a Leica CM 3050 cryostat. Sections were then mounted on Superfrost® plus silanized glass slides. The microscopical observations were made using a Leica DMLB or Orthoplan microscope. Pictures were digitized with a digital DP72 Olympus camera with the Olympus CellD software.

Figure 3A:
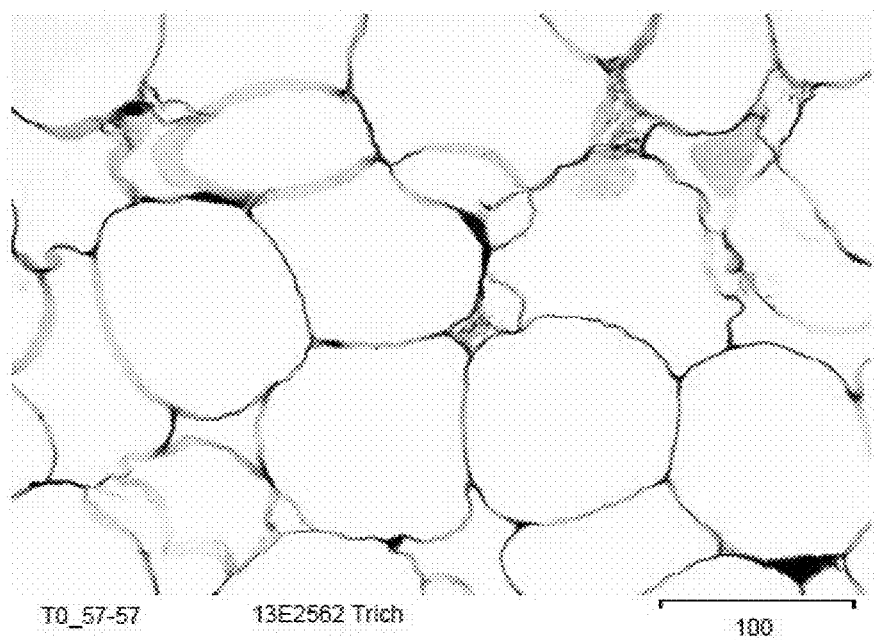
FIGS. 3A-C are digital photos obtained from a microscope of adipocytes at day 0 (A), day 10 no treatment (B), and day 10 treatment with a combination of *Rubus fruticosus* extract, *Argania spinosa* kernel oil, *Coleus barbatus* extract, glycolic acid, and a mixture of caffeine, escin, and algae extract (C).
Figure 3B:
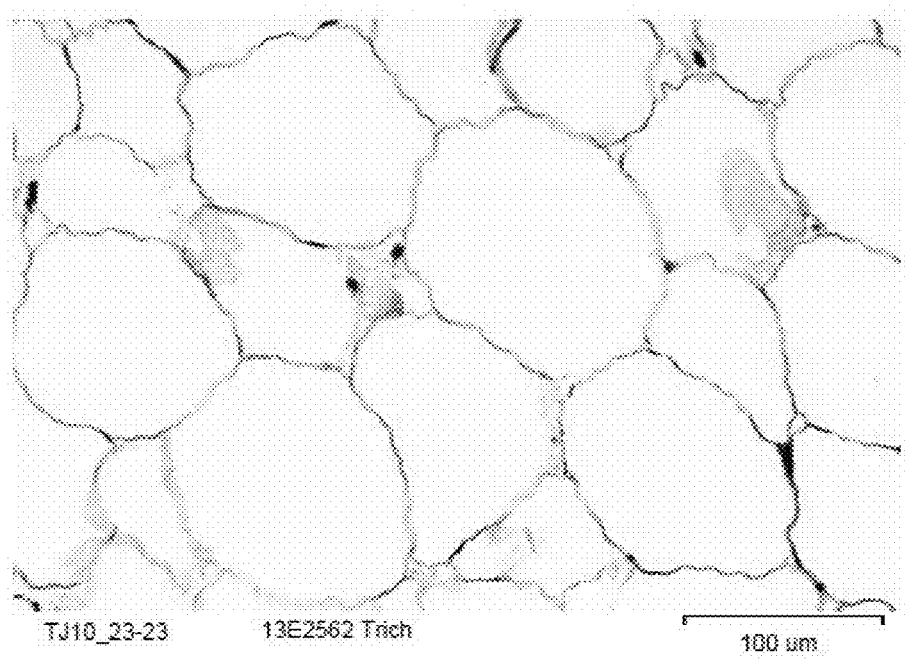
Figure 3C:
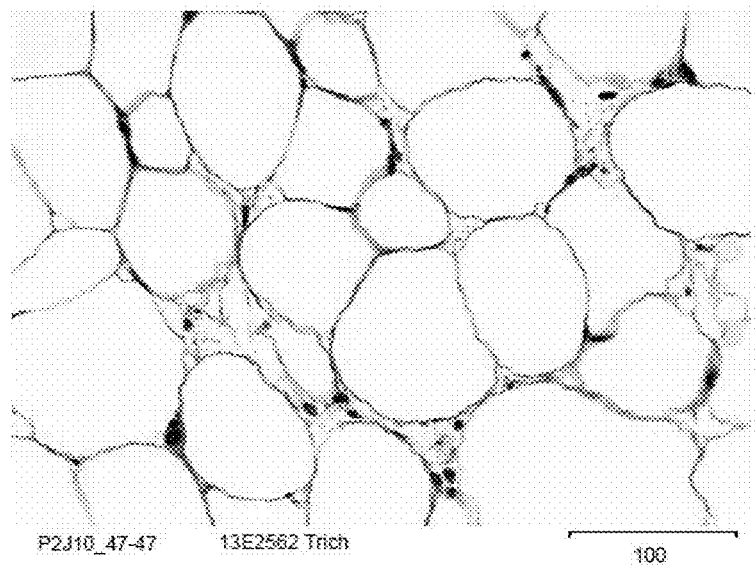

Results:

The lipolytic activity has been evaluated by the average of adipocytes size. The expression of the measures as distribution according to adipocyte size allows to better highlight the variation induced by the different treatments. For each batch, adipocytes have been regrouped according to their equivalent circular diameter. The results are expressed as % of adipocytes belonging to a particular class. In particular, an increase of 16% of the class of adipocytes with an equivalent circular diameter of 0-40 μm was observed, whereas a decrease of 8% of the class with a diameter of 40-160 μm was observed. This confirms that a decrease in the size of adipocytes was observed as larger sized adipocytes decreased, thereby resulting in an increase in the number of smaller sized adipocytes. Table 3 provides a summary of these results. FIGS. 3A, 3B, and 3C illustrate the morphology (by digital microscope) of the cells at day 0, day 10 untreated, and day 10 treated, respectively.

TABLE 3*

| | Untreated | Treated |
|---|---|---|
| Number of adipocytes | 325 | 402 |
| Diameter Max (μm) | 152.1 | 135.0 |
| Diameter Min (μm) | 11.52 | 11.42 |
| Diameter Average (μm) | 59.96 | 54 |
| Diameter Median | 56.14 | 57.1 |
| Distribution of adipocytes (%) in two classes according to the equivalent circular diameter (0 to 40 μm and ≥40 μm) | | |
| % class 0-40 μm | 34.15 | 39.6 |
| % class 40-160 μm | 65.85 | 60.4 |

Example 3

In Vitro Data for Epidermal Thickness and Triglyceride Release

The same combination of actives, in the same amounts, and the same base lotion formulation from Example 1 was also used to test the ability of the combination of ingredients to increase epidermal thickness and triglyceride release from adipocytes. The same type of explants and treatment conditions used in Example 2 were used in this Example 3. The same type of explants and treatment conditions used in Example 2 were used in this Example 3. The results of this study show that epidermal thickness is increased by 21%, and triglyceride release is increased by 207%.

Image Analysis of Epidermis Thickness:

The epidermis thickness was determined by image analysis with software LEICA QWIN. Table 4 provides the results.

TABLE 4*

| | Day 0 | Day 10 |
|---|---|---|
| Thickness (μm) | Average/SD | Average/SD |
| Control (untreated) | 27.0/6.3 | 26.4/7.9 |
| Treated | N/A | 32/12.3 |

Lipid Assay:

After extraction from the culture medium, lipids were assayed by TLC. Lipolytic activity was evaluated by proportions analysis of triglycerides, diglycerides, monoglycerides and free fatty acids. Tables 5-6 provide the results.

TABLE 5*

|  | Day 0 | Day 10 |
| --- | --- | --- |
| Fatty Acids (µg) | Average/SD | Average/SD |
| Control (untreated) | 24.6/6.5 | 21.2.3.3 |
| Treated | N/A | 21.5/3.1 |

TABLE 6*

|  | Day 0 | Day 10 |
| --- | --- | --- |
| Triglycerides (µg) | Average/SD | Average/SD |
| Control (untreated) | 21.9/9.2 | 366.9/109.1 |
| Treated | N/A | 1124.6/251.9 |

Glycerol Assay:

Glycerol was directly assayed on culture medium after lipids extraction by an enzymatic method using the Megazyme K-GCROL kit. Table 7 provides the results.

TABLE 7*

|  | Day 0 | Day 10 |
| --- | --- | --- |
| Glycerol (mg/ml) | Average/SD | Average/SD |
| Control (untreated) | 0.0006/0.0003 | 0.182/0.055 |
| Treated | N/A | 0.204/0.081 |

Example 4

Non-Limiting Examples of Compositions

The compositions in Tables 8-10 are non-limiting compositions that can be used in the context of the present invention.

TABLE 8*

| Ingredient | % Concentration (by weight) |
| --- | --- |
| Phase A | |
| Water | q.s. to 100 |
| Xanthum gum | 0.1 |
| M-paraben | 0.15 |
| P-paraben | 0.1 |
| Citric acid | 0.01 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Active Ingredients** | 5.0 |

*Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**Any of the active ingredients (or combination thereof) described in the specification can be used. For instance, the active ingredients can include Rubus fruticosus leaf extract, Argania spinosa kernel oil, Coleus barbatus extract, glycolic acid, and a mixture of caffeine, escin, and algae extract (e.g., Ascophyllum nodosum extract). Although the total amount of active ingredients in the Table 1 formulation is 5% w/w, it is contemplated that the amount of active ingredients can be increased or decreased to achieve a desired result, where the water amount can be increased/decreased accordingly (e.g., q.s.).

TABLE 9*

| Ingredient | % Concentration (by weight) |
| --- | --- |
| Phase A | |
| Water | q.s. to 100 |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Active Ingredient(s)** | 2.0 |

*Add ingredients in phase A to beaker and heat to 70-75° C. while mixing. Subsequently, add the phase B ingredient with phase A and cool to 30° C. with mixing. Subsequently, add phase C ingredient while mixing.
**Any of the active ingredients (or combination thereof) described in the specification can be used. For instance, the active ingredients can include Rubus fruticosus leaf extract, Argania spinosa kernel oil, Coleus barbatus extract, glycolic acid, and a mixture of caffeine, escin, and algae extract (e.g., Ascophyllum nodosum extract). Although the total amount of active ingredients in the Table 2 formulation is 2% w/w, it is contemplated that the amount of active ingredients can be increased or decreased to achieve a desired result, where the water amount can be increased/decreased accordingly (e.g., q.s.).

TABLE 10*

| Ingredient | % Concentration (by weight) |
| --- | --- |
| Water | 65 |
| Alcohol Denat. | 8.3 |
| Glycerin | 5 |
| Sorbitol | 3.5 |
| Cyclopentasiloxane | 3 |
| Dimethicone | 1.6 |
| Caffeine | 1 |
| Pentaerythrityl Tetraisostearate | 1 |
| Caprylic/Capric Triglyceride | 1 |
| Pentylene Glycol | 1 |
| Ethoxydiglycol | 1 |
| Ammonium Acryloyldimethyltaurate/VP Copolymer | 1 |
| Triethanolamine | 0.8 |
| Argania Spinosa Kernel Oil** | 0.75 |
| Jojoba Esters | 0.75 |
| Glycolic Acid | 0.56 |
| Phenoxyethanol | 0.52 |
| Cetyl Alcohol | 0.5 |
| Dipropylene Glycol | 0.48 |
| Maltodextrin | 0.46 |
| Caprylyl Glycol | 0.41 |
| Cetearyl Alcohol | 0.39 |
| Acrylates/C10-30 Alkyl Acrylate Crosspolymer | 0.30 |
| Xanthan Gum | 0.25 |
| Menthyl Lactate | 0.25 |
| Fragrance | 0.25 |
| Rubus Fruticosus (Blackberry) Leaf Extract** | 0.04 |
| Coleus Barbatus Root Extract** | 0.03 |
| Escin** | 0.003 |
| Ascophyllum Nodosum Extract** | 0.003 |
| Excipients*** | q.s. |

*This formulation is structured as a cream-gel and was prepared by mixing the ingredients together under heat and then allowing the mixture to cool to room temperature (20 to 25° C.) to form the cream-gel structure.
**Argania spinosa kernel oil was from BASF (USA) under the trade name Lipofructyl Argan ®. Rubus fruticosus extract was from Symrise (Germany) under the trade name SymMatrix ®. Coleus barbatus extract was from Actives International (USA) under the trade name Via Pure ® Coleus. Caffeine, escin, and Ascophyllum nodosum extract was a mixture from Rovi GMBH (Germany) under the trade name Rovisome ® F.E.C.
***Additional excipients can be used to modify the rheological or tactile properties of the formula or to include preservative systems as desired. The amounts of these excipients can be varied as desired, including increased, by further modifying the amount of water in the formula.

Figure 4A:
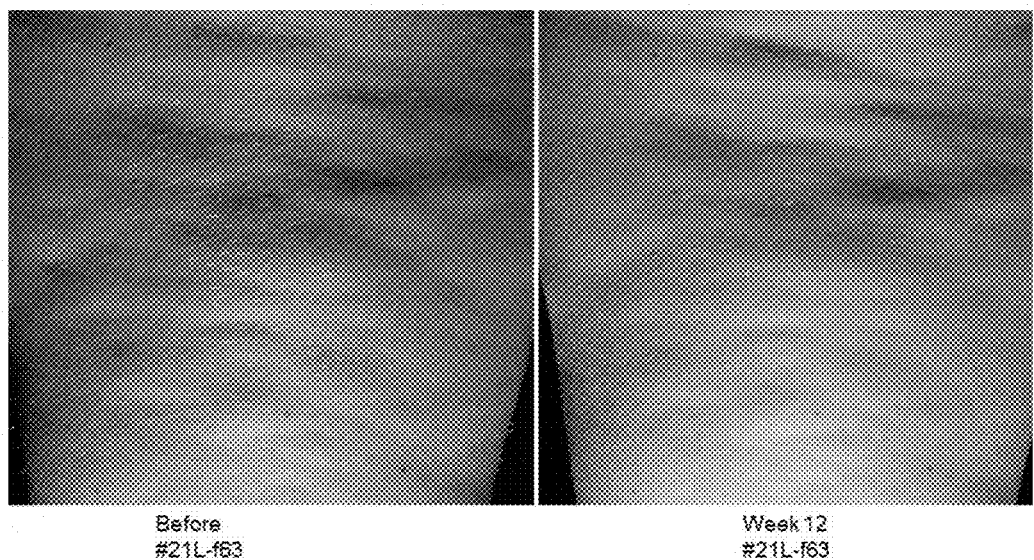
FIGS. 4A-C are digital photos of three different individual's thigh skin before (week 0) and after (week 12) using a composition having the combination of *Rubus fruticosus* extract, *Argania spinosa* kernel oil, *Coleus barbatus* extract, glycolic acid, and a mixture of caffeine, escin, and algae extract.
Figure 4B:
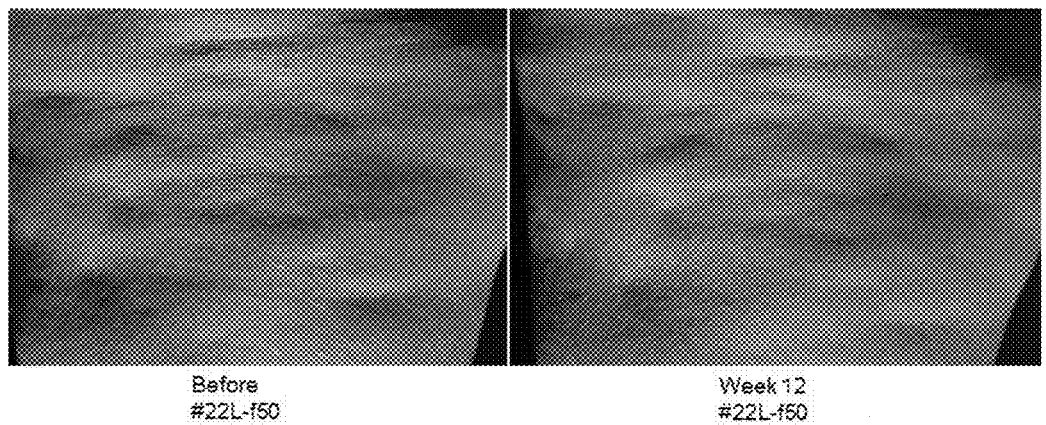
Figure 4C:
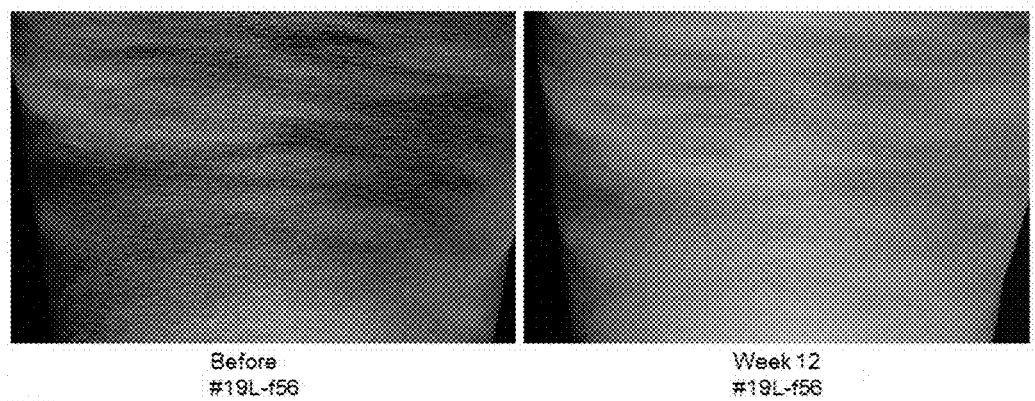

The Table 10 formulation was subjected to a 12 week clinical study to determine the efficacy of the formulation in treating the appearance of cellulite, improving skin texture, and improving skin elasticity and firmness. Forty-five females ("panelists") having an age range between 20-65 used the Table 10 formulation twice per day (AM and PM) for twelve weeks on thighs having the appearance of cellulite and rough skin texture ("targeted area"). Panelists having mild to moderate cellulite on the thighs were selected for this study. The panelists did not use other skin products on their thighs. At day 0, all panelists were tested as the baseline/start point. Clinical evaluations and biophysical measurements were subsequently taken at weeks 3, 8, and 12 of this study. The evaluations included: (1) expert visual grading of cellulite appearance and skin texture (Table 11); (2) panelist measurements concerning skin elasticity and firmness (Table 12); and photographs of three panelists at baseline (week 0 or "Before") and at week 12 (end of study) (see FIGS. 4A-C). The data in Tables 11-12 and in FIGS. 4A-C confirm that the Table 10 composition is clinically shown to improve the appearance of cellulite, skin texture, and elasticity in a person's skin.

TABLE 11

(Expert Visual Grading Data)

| Parameter Graded | % of Panelists Showing Improvement Compared to Baseline [Mean %] | | |
|---|---|---|---|
| | Week 3 | Week 8 | Week 12 |
| Cellulite Appearance | 44 [7] | 71 [13] | 73 [18] |
| Skin Texture/ Smoothness | 75 [32] | 86 [44] | 95 [55] |

TABLE 12

(Panelist Measurement Data)

| Parameter Graded | % of Panelists Showing Improvement Compared to Baseline [Mean %] | | |
|---|---|---|---|
| | Week 3 | Week 8 | Week 12 |
| Skin Elasticity (Ur/Ue) | 69 [10] | NS* | 75 [7] |
| Skin Firmness (Uf) | 67 [5] | 67 [8] | NS* |

*NS: Not significant at 95% confidence level compared to baseline.

Example 5

Additional Assays

In addition to the assays mentioned above, the efficacy of the combination of ingredients disclosed throughout the specification and claims can be determined by using the following assays.

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with a composition of the present invention. Repeat measurements are taken at regular intervals to determine the formula's ability to reduce redness and irritation.

Skin Moisture/Hydration Assay:

Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay with Methods Disclosed in Packman et al. (1978):

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the area of the replicas covered by wrinkles or fine lines was determined.

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay:

In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

ORAC Assay:

Oxygen Radical Absorption (or Absorbance) Capacity (ORAC) of the aromatic skin-active ingredients and compositions can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of the aromatic skin-active ingredients and compositions can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Matrix Metalloproteinase Enzyme Activity (MMP3; MMP9) Assay:

An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methylpentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm ($\varepsilon$=13,600 M−1 cm−1 at pH 6.0 and above 7).

B16 Pigmentation Assay:

Melanogenesis is the process by which melanocytes produce melanin, a naturally produced pigment that imparts color to skin, hair, and eyes. Inhibiting melanogenesis is beneficial to prevent skin darkening and lighten dark spots associated with aging. This bioassay utilizes B16-F1 melanocytes (ATCC), an immortalized mouse melanoma cell line, to analyze the effect of compounds on melanogenesis. The endpoint of this assay is a spectrophotometric measurement of melanin production and cellular viability. B16-F1 melanocytes, can be cultivated in standard DMEM growth medium with 10% fetal bovine serum (Mediatech) at 37° C. in 10% $CO_2$ and then treated with any one of the active ingredients, combination of ingredients, or compositions having said combinations disclosed in the specification for 6 days. Following incubation, melanin secretion was measured by absorbance at 405 nm and cellular viability was quantified.

Collagen Stimulation Assay:

Collagen is an extracellular matrix protein critical for skin structure. Increased synthesis of collagen helps improve skin firmness and elasticity. This bioassay can be used to examine the effect of any one of the active ingredients, combination of ingredients, or compositions having said combinations disclosed in the specification on the production of procollagen peptide (a precursor to collagen) by human epidermal fibroblasts. The endpoint of this assay is a spectrophotometric measurement that reflects the presence of procollagen peptide and cellular viability. The assay employs the quantitative sandwich enzyme immunoassay technique whereby a monoclonal antibody specific for procollagen peptide has been pre-coated onto a microplate. Standards and samples can be pipetted into the wells and any procollagen peptide present is bound by the immobilized antibody. After washing away any unbound substances, an enzyme-linked polyclonal antibody specific for procollagen peptide can be added to the wells. Following a wash to remove any unbound antibody-enzyme reagent, a substrate solution can be added to the wells and color develops in proportion to the amount of procollagen peptide bound in the initial step using a microplate reader for detection at 450 nm. The color development can be stopped and the intensity of the color can be measured. Subconfluent normal human adult epidermal fibroblasts (Cascade Biologics) cultivated in standard DMEM growth medium with 10% fetal bovine serum (Mediatech) at 37° C. in 10% $CO_2$, can be treated with each of the combination of ingredients or compositions having said combinations disclosed in the specification for 3 days. Following incubation, cell culture medium can be collected and the amount of procollagen peptide secretion quantified using a sandwich enzyme linked immuno-sorbant assay (ELISA) from Takara (#MK101).

Tumor Necrosis Factor Alpha (TNF-α) Assay:

The prototype ligand of the TNF superfamily, TNF-α, is a pleiotropic cytokine that plays a central role in inflammation. Increase in its expression is associated with an up regulation in pro-inflammatory activity. This bioassay can be used to analyze the effect of any one of the active ingredients, combination of ingredients, or compositions having said combinations disclosed in the specification on the production of TNF-α by human epidermal keratinocytes. The endpoint of this assay can be a spectrophotometric measurement that reflects the presence of TNF-α and cellular viability. The assay employs the quantitative sandwich enzyme immunoassay technique whereby a monoclonal antibody specific for TNF-α has been pre-coated onto a microplate. Standards and samples can be pipetted into the wells and any TNF-α present is bound by the immobilized antibody. After washing away any unbound substances, an enzyme-linked polyclonal antibody specific for TNF-α can be added to the wells. Following a wash to remove any unbound antibody-enzyme reagent, a substrate solution can be added to the wells and color develops in proportion to the amount of TNF-α bound in the initial step using a microplate reader for detection at 450 nm. The color development can be stopped and the intensity of the color can be measured. Subconfluent normal human adult keratinocytes (Cascade Biologics) cultivated in EpiLife standard growth medium (Cascade Biologics) at 37° C. in 5% $CO_2$, can be treated with phorbol 12-myristate 13-acetate (PMA, 10 ng/ml, Sigma Chemical, #P1585-1MG) and any one of the active ingredients, combination of ingredients, or compositions having said combinations disclosed in the specification for 6 hours. PMA has been shown to cause a dramatic increase in TNF-α secretion which peaks at 6 hours after treatment. Following incubation, cell culture medium can be collected and the amount of TNF-α secretion quantified using a sandwich enzyme linked immuno-sorbant assay (ELISA) from R&D Systems (#DTA00C).

Antioxidant (AO) Assay:

An in vitro bioassay that measures the total anti-oxidant capacity of any one of the ingredients, combination of ingredients, or compositions having said combinations disclosed in the specification. The assay relies on the ability of antioxidants in the sample to inhibit the oxidation of ABTS® (2,2'-azino-di-[3-ethylbenzthiazoline sulphonate]) to ABTS®+ by metmyoglobin. The antioxidant system of living organisms includes enzymes such as superoxide dismutase, catalase, and glutathione peroxidase; macromolecules such as albumin, ceruloplasmin, and ferritin; and an array of small molecules, including ascorbic acid, α-tocopherol, β-carotene, reduced glutathione, uric acid, and bilirubin. The sum of endogenous and food-derived antioxidants represents the total antioxidant activity of the extracellular fluid. Cooperation of all the different antioxidants provides greater protection against attack by reactive oxygen or nitrogen radicals, than any single compound alone. Thus, the overall antioxidant capacity may give more relevant biological information compared to that obtained by the measurement of individual components, as it considers the cumulative effect of all antioxidants present in plasma and body fluids. The capacity of the antioxidants in the sample to prevent ABTS oxidation is compared with that of Trolox, a water-soluble tocopherol analogue, and is quantified as molar Trolox equivalents. Anti-Oxidant capacity kit #709001 from Cayman Chemical (Ann Arbor, Mich. USA) can be used as an in vitro bioassay to measure the total anti-oxidant capacity of each of any one of the active ingredients, combination of ingredients, or compositions having said combinations disclosed in the specification. The protocol can be followed according to manufacturer recommendations. The assay relied on antioxidants in the sample to inhibit the oxidation of ABTS® (2,2'-azino-di-[3-ethylbenzthiazoline sulphonate]) to ABTS®+ by metmyoglobin. The capacity of the antioxidants in the sample to prevent ABTS oxidation can be compared with that Trolox, a water-soluble tocopherol analogue, and was quantified as a molar Trolox equivalent.

Mushroom Tyrosinase Activity Assay:

In mammalian cells, tyrosinase catalyzes two steps in the multi-step biosynthesis of melanin pigments from tyrosine (and from the polymerization of dopachrome). Tyrosinase is localized in melanocytes and produces melanin (aromatic quinone compounds) that imparts color to skin, hair, and eyes. Purified mushroom tyrosinase (Sigma) can be incubated with its substrate L-Dopa (Fisher) in the presence or absence of each of the active ingredients, any one of the combination of ingredients, or compositions having said combinations disclosed in the specification. Pigment formation can be evaluated by colorimetric plate reading at 490 nm. The percent inhibition of mushroom tyrosinase activity can be calculated compared to non-treated controls to determine the ability of test ingredients or combinations thereof to inhibit the activity of purified enzyme. Test ingredient inhibition can be compared with that of kojic acid (Sigma).

Cyclooxygenase (COX) Assay:

An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygenase enzyme (COX-1 or COX-2). According to manufacturer instructions, purified enzyme, heme and test ingredients can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test ingredients to inhibit the activity of purified enzyme.

Lipoxygenase (LO) Assay:

An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives, that are subsequently converted to leukotirenes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and mixtures incubated for an additional 10 min at room temperature. Colorimetric substrate can be added to terminate catalysis and color progression was evaluated by fluorescence plate reading at 490 nm. The percent inhibition of lipoxygenase activity can be calculated compared to non-treated controls to determine the ability of each of the active ingredients, any one of the combination of ingredients, or compositions having said combinations disclosed in the specification to inhibit the activity of purified enzyme.

Elastase Assay:

EnzChek® Elastase Assay (Kit# E-12056) from Molecular Probes (Eugene, Oreg. USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, chloromethyl ketone, can be used as a selective, collective inhibitor of elastase when utilizing the EnzChek Elastase Assay Kit for screening for elastase inhibitors.

Oil Control Assay:

An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

REFERENCES

The following references, to the extent that they provide exemplary procedural or other details supplementary to those set forth herein, are specifically incorporated herein by reference.

Cao et al. 1993.
International Cosmetic Ingredient Dictionary and Handbook, 12th Edition, 2008 ("CTFA"), Volume 2 page 2399
International Cosmetic Ingredient Dictionary and Handbook, 12th Edition, 2008 ("CTFA"), Volume 1 page 198, page 655
International Cosmetic Ingredient Dictionary and Handbook, 4th Edition, 1991 ("CTFA"), pp. 12 and 80

Khan et al., *J. Am. Acad. Dermatol.* 62:361-70, 2010.
Kreuter, 1998.
McCutcheon's, 1986.
Packman et al. 1978.
U.S. Pat. No. 2,798,053
U.S. Pat. No. 3,755,560
U.S. Pat. No. 4,421,769
U.S. Pat. No. 4,509,949
U.S. Pat. No. 4,599,379
U.S. Pat. No. 4,628,078
U.S. Pat. No. 4,835,206
U.S. Pat. No. 4,849,484
U.S. Pat. No. 5,011,681
U.S. Pat. No. 5,087,445
U.S. Pat. No. 5,100,660
U.S. Pat. No. 5,411,744
U.S. Pat. No. 6,203,802
U.S. Pat. No. 6,387,398
U.S. Publication No. 2004/0109905
U.S. Publication No. 2005/0163880

The invention claimed is:

1. A method for reducing the appearance of cellulite or improving the texture of skin in a target region of skin that has cellulite or rough skin texture, the method comprising topically applying a composition to the target region that includes an effective amount of a mixture of caffeine, escin, and an aqueous-alcoholic extract from *Ascophyllum nodosum*, wherein topical application of the composition reduces the appearance of cellulite or improves the texture of the skin.

2. The method of claim 1, wherein the composition further comprises effective amounts of *Rubus fruticosus* extract, *Argania spinosa* kernel oil, *Coleus barbatus* extract, and glycolic acid.

3. The method of claim 2, wherein the effective amounts are 0.001 to 10% by weight of the mixture of caffeine, escin, and the aqueous-alcoholic extract from *Ascophyllum nodosum*, 0.001 to 10% by weight of the aqueous-alcoholic extract from *Rubus fruticosus* leaf, 0.001 to 10% by weight of *Argania spinosa* kernel oil, 0.001 to 10% by weight of the *Coleus barbatus* root extract, and 0.001 to 10% by weight of glycolic acid.

4. The method of claim 2, wherein the composition increases skin firmness or elasticity in said target region.

5. The method of claim 2, wherein the composition increases lipolysis in adipocytes.

6. The method of claim 2, wherein the composition decreases maturation of fat cells.

7. The method of claim 2, wherein the target region comprises a dimple, and wherein the composition reduces the appearance of the dimple.

8. The method of claim 7, wherein the composition reduces the difference between the peak and valley of the dimple.

9. The method of claim 2, wherein the composition decreases the size of adipocytes in the target region.

10. The method of claim 9, wherein the composition decreases the size of adipocytes in the target region having a diameter of equal to or greater than 40 μm or have a diameter between 40-160 μm.

11. The method of claim 10, wherein between 5 and 20% of the adipocytes in the target region having a diameter of equal to or greater than 40 μm or have a diameter between 40-160 μm are decreased in size.

12. The method of claim 2, wherein the composition increases the epidermal thickness of skin in the target region between 5 and 50%.

13. The method of claim 2, wherein the composition increases triglyceride release from adipocytes in the target region.

14. The method of claim 1, wherein the composition is formulated as a cream, lotion, or gel.

15. The method of claim 1, wherein the composition is formulated as an emulsion.

16. The method of claim 1, wherein the skin is leg skin, arm skin, torso skin, or skin in the pelvic region.

17. The method of claim 16, wherein the composition is applied to the skin and remains on the skin for at least 5 minutes after topical application.

18. The method of claim 1, wherein the mixture of caffeine, escin, and the aqueous-alcoholic extract is not encapsulated in nanoparticles.

* * * * *